United States Patent [19]

Van Wyk et al.

[11] Patent Number: 5,128,164
[45] Date of Patent: *Jul. 7, 1992

[54] COMPOSITION FOR HUMAN CONSUMPTION CONTAINING 3-(1-AMINO-1,3-DICARBOXY-3-HYDROXY-BUT-4-YL)-INDOLE COMPOUNDS

[75] Inventors: Pieter J. Van Wyk, Nelspruit; Louis G. J. Ackerman, Pretoria, both of South Africa

[73] Assignee: South African Inventions Development Corporation, Pretoria, South Africa

[*] Notice: The portion of the term of this patent subsequent to Dec. 4, 2007, has been disclaimed.

[21] Appl. No.: 686,269

[22] Filed: Apr. 15, 1991

Related U.S. Application Data

[63] Continuation of Ser. No. 449,568, Dec. 12, 1989, abandoned, which is a continuation-in-part of Ser. No. 207,066, Jun. 15, 1988, Pat. No. 4,975,298.

[30] Foreign Application Priority Data

Jun. 15, 1987 [ZA] South Africa ............. 87/4288
Jun. 15, 1987 [ZA] South Africa ............. 87/4289
Jun. 15, 1987 [ZA] South Africa ............. 87/4290

[51] Int. Cl.$^5$ ............................................. A23L 1/236
[52] U.S. Cl. ..................................... 426/548; 549/496
[58] Field of Search ............................................. 426/548

[56] References Cited

U.S. PATENT DOCUMENTS 3,535,336 4/1970 Kornfeld ............................. 549/496

Primary Examiner—Joseph Golian
Attorney, Agent, or Firm—Ladas & Parry

[57] ABSTRACT

The invention provides compositions for human consumption containing, as a sweet tasting constituent, a compound of the formula:

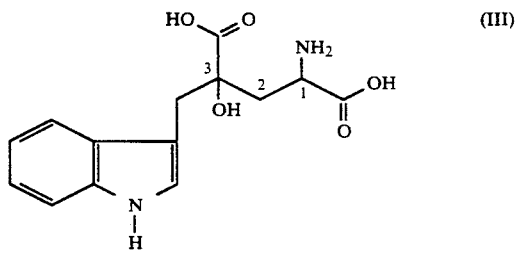

and which is:
3-(1-amino-,3-dicarboxy-3-hydroxy-but-4-yl)-indole, including the isomers, salts and specified internal condensation derivatives thereof, and in particular those which have enhanced sweetening powers relatively to sucrose and which are useful as sweeteners for foods and beverages.

26 Claims, No Drawings

COMPOSITION FOR HUMAN CONSUMPTION CONTAINING 3-(1-AMINO-1,3-DICARBOXY-3-HYDROXY-BUT-4-YL)-INDOLE COMPOUNDS

CROSS-REFERENCE TO RELATED APPLICATION

This application is a continuation of U.S. patent application Ser. No. 07/449,568 filed on Dec. 12, 1989 now abandoned, which was a continuation-in-part of U.S. patent application Ser. No. 07/207,066 filed on Jun. 15, 1988 which was issued as U.S. Pat. No. 4,975,298 on Dec. 4, 1990.

BRIEF SUMMARY OF THE INVENTION

This invention refers to a substituted butane and to salts and derivatives thereof.

Broadly the invention provides 1-amino-1,3-dicarboxy-3-hydroxy substituted butanes according to the general formula (I):

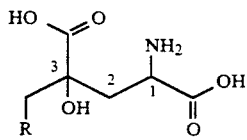

and the invention also provides functional derivatives thereof and salts thereof in which formula R is an aryl or heterocyclic group, a straight chain alkyl, branched chain alkyl or cycloalkyl group, or an aralkyl group, optionally substituted.

The invention extends in particular to the acid addition salts and functional derivatives thereof, which are:

the ammonium, amine, alkali metal (e.g., sodium or potassium), alkali earth metal (e.g., calcium or magnesium) and other metals salts of the acid moieties in the 1 and/or 3 positions;

the ester, amide and substituted amide moieties of the carboxyl groups in the 1 and/or 3 positions; and the acyl and aryl derivatives and the acid (organic and inorganic) salts of the amino-nitrogen group in the 1 position.

The invention includes all stereoisomers with regard to the two chiral centres in the structural formula.

Specific examples for R are phenyl, naphthyl, indolyl, benzofuryl, furyl, thienyl, pyridyl, methyl, ethyl, propyl, butyl, cyclohexyl, or benzyl.

The compounds are promising for use as sweetening agents or intermediates in the preparation of other compounds of the above general formula.

In preferred compounds according to the invention, R is an aryl, substituted aryl, heterocyclic, substituted heterocyclic, cycloalkyl or substituted cycloalkyl group. Particularly preferred compounds in accordance with the invention are 3-(1-amino-1,3-dicarboxy-3-hydroxy-but-4-yl)-indole compounds in accordance with the general formula (II):

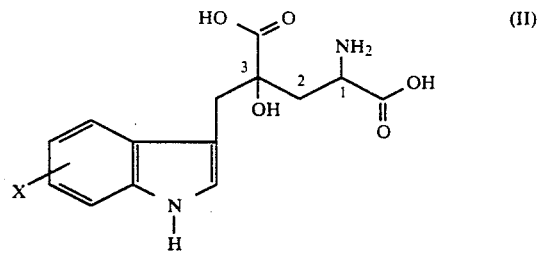

in which X is aryl, alkyl or arylkyl, optionally substituted, halo, trihaloalkyl, hydroxy or carboxy, or, preferably, hydrogen.

A particularly preferred compound in accordance with the invention is a compound of formula (I) in which X is hydrogen, i.e., (III):

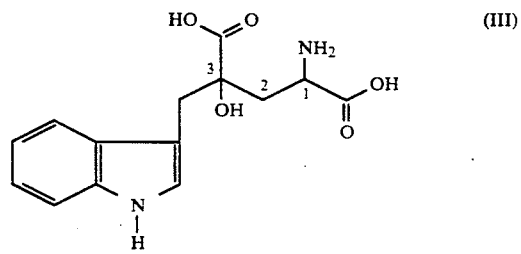

which has enhanced sweetening powers relative to sucrose. This compound is a high-intensity low calorie sweetener and can be isolated from the roots of the plant *Schlerochiton ilicifolius*, found in the Northern Transvaal region of South Africa, and it can be used as a sweetener for human consumption.

When the indole of said formula (III) in the acid form is sufficiently pure, it exists as a crystalline solid having a melting point of 247°-265° C., with decomposition. The indole in its acid form is soluble with difficulty in water.

This compound, i.e., 3-(1-amino-1,3-dicarboxy-3-hydroxy-but-4-yl)-indole (which can also be called 4-hydroxy-4-(3-indolemethyl)-glutaric acid, depending on the nomenclature employed) can be extracted with water from the bark of the roots of *Schlerochiton ilicifolius*, and, after filtration, washing and freeze drying has been found to have a sweetness several hundred times that of sucrose.

The invention accordingly extends also to a method of obtaining a compound in accordance with formula (III) as defined above, which comprises grinding the bark of the roots of *Schlerochiton ilicifolius*, soaking the ground bark in water to obtain an extract thereof, subjecting the extract to cation exchange chromatography to purify it, and drying the cation-exchanged extract.

The concentration of the compound of formula (III) present in the dried bark, expressed as the indole in its acid form, has been found to be about 0.007% by mass. The bark in its raw undried form comprises at least 60% by mass of water so that the concentration of said indole in the wet bark is no more than 0.0042% by mass. In turn, the bark (whether on a wet basis or a dry basis) makes up about 40% by mass of the root, so that said indole is present in the raw undried root in a concentration of no more than about 0.0017% by mass.

In contrast, the minimum concentration or purity of the indole of formula (III) or its salts or derivatives for utility as a sweetener is about 0.7% by mass (i.e., about 500 times more concentrated than in the undried raw root), and this concentration for utility is preferably at least 1% by mass and more preferably at least 10% by mass.

Two particular derivatives of the compound of formula (III) exists, which are the products of internal condensation of said indole compound, and are members of the group consisting of:

(i) a lactone of the formula (IV):

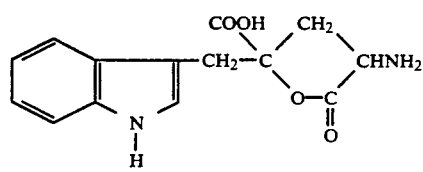

and (ii) a lactam of the formula (V):

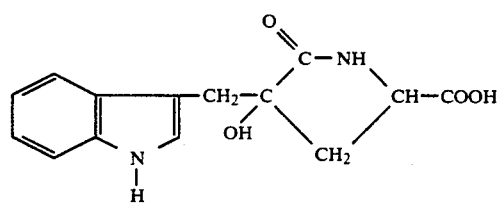

It is believed that the lactone of formula (IV) and the lactam of formula (V) are not present in the plant root bark because the pH in the plant root bark is inappropriate for the existence of these condensation derivatives.

The lactone and lactam can form revesibly, depending on the pH, in an aqueous solution of said indole compound, by condensations according to the following reactions respectively:

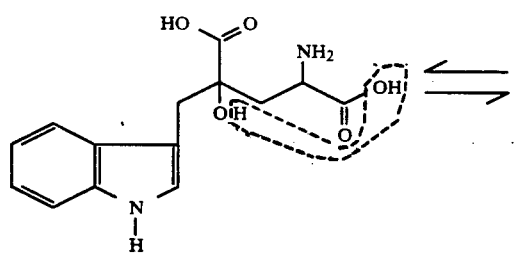

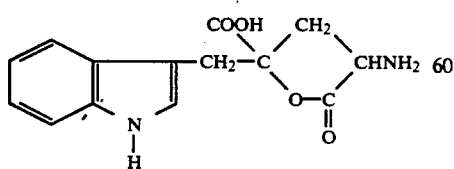

and

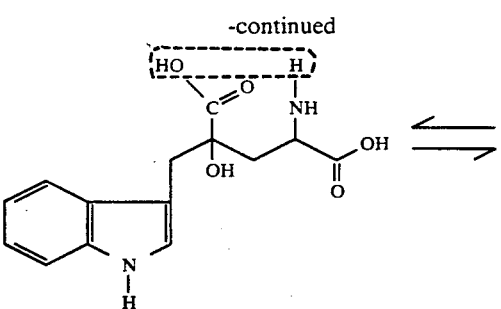

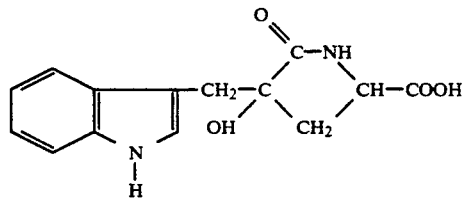

When the lactone of formula (IV) or the lactam of formula (V) is exposed to the appropriate pH in an aqueous solution, the condensation can reverse almost completely to provide a solution of the indole starting material.

Furthermore, the salts of compound (III) at the 1 and/or 3 positions can easily be obtained, such as ammonium, alkylammonium, sodium, potassium, calcium and magnesium salts, in particular. For use as sweeteners it is expected that these salts, in addition to compound (III) itself, will be of particular importance.

The salts and condensation products of formula (IV) and (V) exist as amorphous solids, and at least the ammonium, amine, sodium, potassium, calcium and magnesium addition salts of these products are readily soluble in water. The sodium salt exhibits an optical rotation of $-29.7°$. when dissolved in water at a concentration of 10 mg/ml.

Thus, in accordance with the present invention, there is provided a compound of the formula (III):

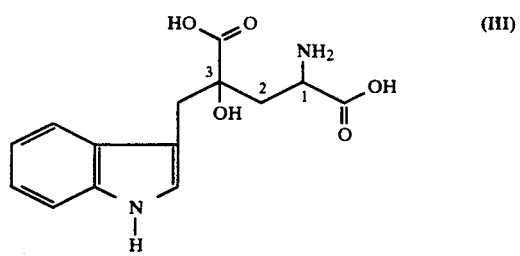

and which is 3-(1-amino-1,3-dicarboxy-3-hydroxy-but-4-yl)-indole or a salt thereof at the 1 and/or 3 positions, or a derivative thereof which is an internal condensation product thereof selected from the group consisting of the lactone of the formula (IV):

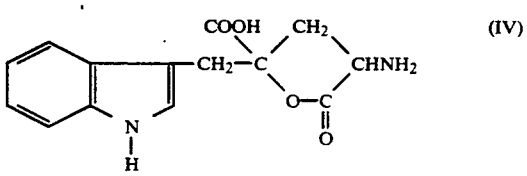

and the lactam of the formula (V):

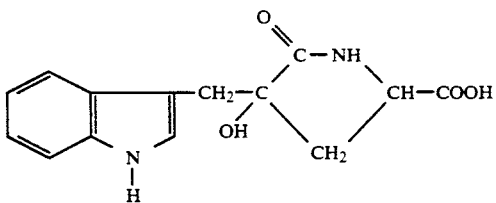

In accordance with this invention, the compounds are present at a concentration of at least 7 g/kg, or at least 0.7% pure.

DETAILED DESCRIPTION

The invention extends in particular to said 3-(1-amino-1,3-dicarboxy-3-hydroxy-but-4-yl)-indole of formula (III), and to a salt at the 1 and/or 3 positions of said 3-(1-amino-1,3-dicarboxy-3-hydroxy-but-4-yl)-indole of formula (III) and which is a salt selected from the group consisting of the ammonium, alkylammonium, sodium, potassium, calcium and magnesium salts thereof. The invention also extends particularly to a derivative of said 3-(1-amino-1,3-dicarboxy-3-hydroxy-but-4-yl)-indole of formula (III), and which is a condensation product thereof selected from the group consisting of the lactone of the formula (IV):

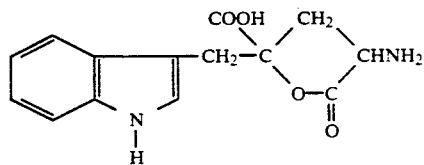

and the lactam of the formula (V):

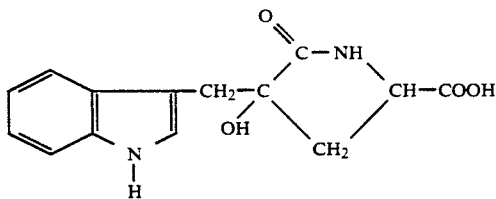

As will emerge from the Examples set out hereunder, a particular stereoisomer of the indole of formula (III) has been found in naturally occurring plant material, and that stereoisomer, i.e., the stereoisomer of said 3-(1-amino-1,3-dicarboxy-3-hydroxy-but-4-yl)-indole of formula (III) which is found in the roots of the plant *Schlerochiton ilicifolius*, or a salt or a said condensation product of said stereoisomer is preferred for this reason.

The invention will now be described in more detail with reference to the following non-limiting illustrative Examples.

EXAMPLE 1

Freshly harvested roots of *Schlerochiton ilicifolius* were freeze dried and debarked, and the bark was ground in a hammer mill. The ground bark was extracted with water, filtered and freeze dried to obtain a dark brown, earthy smelling amorphous mass. This mass was redissolved in water and reacted with a cation resin in the acid form, i.e., "Biorad" AG50W x8 in the HCl form available from Bio-Rad Laboratories, Richmond, Calif., U.S.A.

The resin was washed several times with water and the compounds bound to the resin were liberated from the resin by means of a 5% m/m aqueous ammonia solution. The eluate so obtained was freeze dried and subjected to aqueous gel filtration using "Biogel" P4 available from Bio-Rad Laboratories, followed by "Sephadex" G10 available from Pharmacia, Uppsala, Sweden. A product was obtained which, after freeze drying, was pure on thin layer chromatography and was sweet tasting. Its structure was deduced from nuclear magnetic resonance tests ($^1H_{nmr}$ and $^{13}C_{nmr}$) to be according to formula (III) hereinabove.

The sweetness of the product was determined by a procedure which involved the tasting of the compound by a taste panel trained for tasting sweet substances. The object of the investigation was to determine the sweetness of the indole compound in accordance with formula (III) relative to the sweetness of sucrose in terms of recognition threshold concentrations. In this regard, recognition threshold concentrations are the concentrations at which a certain taste stimulus can be identified, as opposed to absolute threshold concentrations, which are the minimum concentrations at which such stimulus can be detected (as opposed to identified), i.e., the minimum concentration at which a solution can be classified as being different from pure water.

The product was tasted by a taste panel trained for tasting sweet compounds and was found to be up to 800 times sweeter than sucrose. The procedure used was described in Viljoen A.J. and Lubbe A.—"The Determination of the Relative Sweetness at Threshold Levels of Sucrose and a New Natural Sweetener." Internal Report: National Food Research Institute of the South African Council for Scientific and Industrial Research (Mar. 6, 1984). The test involved determining the sweetness of the compound relative to sucrose at the threshold value at which sweetness is recognizable.

The panel members who were used for the threshold determination were chosen from a total of 32 people by means of screening tests. 10 panel members were selected on the basis of their ability to test and evaluate sweetness using the methods of Vaisey Genzer et al. (Vaisey Genzer, M. and Moskowitz, H. 1977. S. Sensory Response to Food. A sensory Workshop in collaboration with J. Solms and H. J. Roth. Foster Verlag AG, Zurich).

The selected panelists were subjected to an intensive training programme in order to improve their ability to detect and interpret sweetness at threshold concentrations. The method of Jellinek (Jellinek G. 1964). Introduction and Critical Review of Modern Methods of Sensory Analysis (odour, taste and flavour evaluation) with special emphasis on descriptive sensory analysis (flavour profile method). J. Nutr. Diet. 1, 219–260.) were used in this regard and can be described as follows:

Each panelist was presented with a range of solutions with increasing concentrations of sucrose in distilled water. The panel member had to indicate in which solution that person was able to identify sweetness. This concentration was taken as the recognition threshold concentration. Because of possible interference of chlorine with the determinations, distilled water was used for preparation of sweetness solutions and was de-ionized to remove trace amounts of any chlorine or any organic compounds present. Removal of organic compounds was verified by high pressure liquid chromatography. The concentrations of sucrose used in the various solutions are given in the following table, Table 1.

TABLE 1

| Solution No. | Concentration ($\times 10^{-3}$ M) |
|---|---|
| 1 | 0.2 |
| 2 | 0.4 |
| 3 | 0.8 |
| 4 | 1.6 |
| 5 | 3.2 |
| 6 | 6.4 |
| 7 | 12.8 |

This test was repeated ten times in order to ascertain the accuracy of the panel results. Another series of sucrose solutions of different concentrations was presented to the panelists, who had to determine the sweetness of every solution relative to a control. With this exercise the panelists could be taught to estimate the relative strengths of sensations of sweetness. The concentrations, on a molar basis, were respectively: 0.06 0.125 0.25 and 0.5 with the control concentration being 0.25.

After an initial training period of 2 months, the panelists were asked to determine the threshold concentration of the sweetener in accordance with formula (III) in pure water of the type described above. This was conducted in the fashion described above for sucrose.

Although the panel was believed to have been trained, it remained necessary to hold training sessions, using sucrose solutions during the evaluation of the new sweetener. The reasons for this were that, initially the panel tended to determine absolute threshold, rather than recognition threshold, and where some chlorine was present in distilled water, its role had to be eliminated or compensated for.

The following table, Table 2, represents the results of six final taste sessions conducted by the panelists, in order to determine the recognition threshold values for sucrose in water.

TABLE 2

| Panelist | Taste Session Number | | | | | |
|---|---|---|---|---|---|---|
| | 1 | 2 | 3 | 4 | 5 | 6 |
| 1 | 6 | 6 | 7 | 7 | 6 | 6 |
| 2 | 5 | 6 | 5 | 6 | 6 | 6 |
| 3 | 6 | 5 | 6 | 5 | 7 | 7 |
| 4 | 2 | 7 | 6 | 6 | 6 | 6 |
| 5 | 6 | 4 | 6 | 7 | 6 | 6 |
| 6 | 4 | 6 | 6 | 6 | 6 | 7 |
| 7 | 5 | 4 | 5 | 5 | 6 | 7 |
| 8 | 7 | 6 | 4 | 6 | 6 | 6 |
| 9 | 7 | 6 | 6 | 7 | 6 | 6 |
| 10 | — | — | 4 | 6 | 5 | 5 |

In the above table, in the columns under the heading giving the tasting session number, are given the solution numbers in accordance with Table 1 at which the panelists detected sweetness, i.e., their recognition threshold values.

An improvement with time by the panelists could be discerned from Table 2 and as the panel members became more trained the recognition threshold values tended to be more constant. From Table 2 it can be deduced that the recognition threshold value for sucrose as determine by the panel in question was between 0.0064 and 0.0128 on a molar basis. This result implies that the recognition threshold value is between 0.219 and 0.438% (g/ml) which corresponds well with values cited in literature. Thus, for example, Spencer (Spencer H. W., 1971. Taste Panels and the Measurement of Sweetness. In Sweetness and Sweeteners. Edited by Birch, G. G., Green, L. F. and Coulson, C. B. Applied Sci. Publ. London. ISBN 085334-503-1.) The results indicated that the panel could determine the threshold value of sucrose with adequate accuracy and that the panel could be consistent during different taste sessions.

The test illustrated in Table 2 was repeated with the sweetener in accordance with the invention in accordance with formula (III) in pure water. Samples were prepared having concentrations ranging between 0.2 and 0.35 mg/100 ml with six equal increments in concentration. Four tasting sessions were held, and the results are set out in the following table, Table 3.

TABLE 3

| Panelist | Tasting session number | | | |
|---|---|---|---|---|
| | 1 | 2 | 3 | 4 |
| 1 | 0.3 | 0.25 | 0.27 | 0.29 |
| 2 | 0.25 | 0.3 | 0.22 | 0.20 |
| 3 | 0.3 | 0.25 | 0.25 | 0.27 |
| 4 | 0.3 | — | 0.27 | 0.27 |
| 5 | 0.3 | 0.3 | — | 0.3 |
| 6 | 0.3 | 0.45 | 0.3 | 0.3 |
| 7 | 0.2 | 0.2 | — | — |
| 8 | 0.4 | 0.35 | 0.25 | 0.25 |
| 9 | 0.25 | 0.3 | 0.29 | 0.29 |
| 10 | 0.25 | 0.25 | 0.25 | 0.27 |

In the above table in the columns under the various testing session numbers, the concentrations of recognition threshold value in mg/100 ml are indicated.

A slight variance in results was noted, but if it is taken into account that the recognition threshold concentration varied between 0.0002% and 0.0003% m/v (g/ml) the variation in results was relatively small.

It was calculated from the above results that the sweetness of the compound in accordance with the invention with formula (III) at the recognition threshold value was about 800 times that of sucrose in terms of m/v (g/ml) (calculated on the lowest detection value of sucrose in order to compensate for any possible faults in the use of the panel).

The above tests applied particularly to recognition threshold values, for both sucrose and the compound in accordance with the invention, and the assumption that the same comparison will hold true for higher concentrations is not necessarily valid. As is evident from Pangborn (Pangborn, R. M. 1981. A Critical Review of Threshold Intensity and Descriptive Analyses in Flavor Research in Flavour. 1981 Edited by Schreier P. 3-32. Walter de Gruyter & Co. Berlin; New York. ISPN3-11-008441-4), further tests must be conducted in order to determine whether or not the relative sweetness of sucrose and the sweetener in accordance with the invention are the same at higher concentrations, but due to a shortage of test material these tests were not attempted.

EXAMPLE 2

A laboratory synthesis method has been developed by the Applicant for synthesizing the indole of formula (III) and its salts and its derivatives of formulae (IV) and (V). In particular the synthesis leads to the potassium salt at both the 1 and/or 3 positions of the indole of formula (III), from which it is trivial to obtain the indole itself or other salts by cation exchange, or the derivatives of formula (IV) and (V) by altering the pH in an aqueous solution as described above.

The synthesis involves a number of starting materials and intermediate compounds, and a number of synthesis steps. For ease of reference, a preliminary listing of numbered starting materials and intermediate compounds is provided hereunder, and these compounds will be referred to by number in the synthesis steps which follow:

LIST OF COMPOUNDS

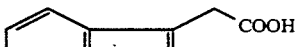  1

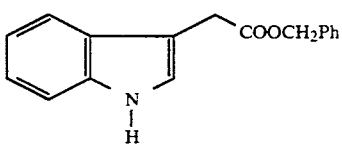  2

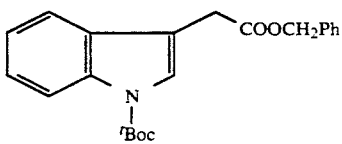  3

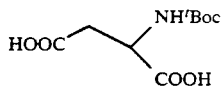  4

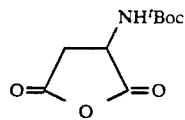  5

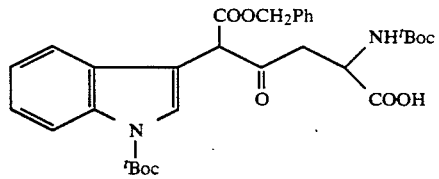  6

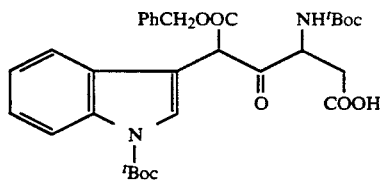  7

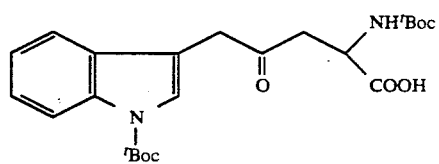  8

-continued
LIST OF COMPOUNDS

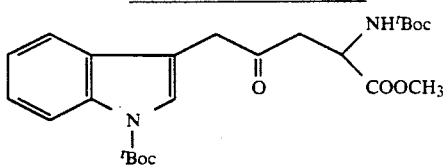  9

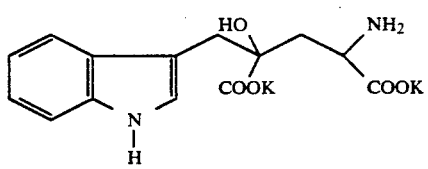  10

EXPERIMENTAL

Melting points were recorded on a Reichert apparatus. I.R. spectra were obtained on a Perkin-Elmer-257 or 883 spectrophotometer as liquid films. $^1$H-NMR spectra were recorded on a Varian EM-390 operating at 90 MHz or a Bruker WM 500 spectrometer. Mass spectra were obtained on a Varian MAT 212 instrument. Silica was used for chromatography throughout; TLC plates were Merck silica gel 60 F254, and flash chromatography was performed with Merck silica gel 60 (230-400 mm) as described by Still. The reactions were conveniently followed by TLC, and the compounds were visualized by the CeSO$_4$ spray reagent.

The following synthesis stages, numbers (1) to (8) were carried out:

(1) Preparation of indole-3-acetic acid benzyl ester-2

(a) Preparation of benzyl dimethyl anilinium hydroxide

A mixture of freshly distilled N,N-dimethyl aniline (52 ml, 0.41 mol) and benzyl chloride (47 ml, 0.41 mol) was allowed to stand for several days at room temperature. The separated crystals of benzyl dimethyl anilinium chloride were filtered and washed with anhydrous ether. The chloride salt (14.3 g, 0.054 mol) and silver oxide (13.4 g, 0.057 mol) were then stirred in anhydrous methanol (300 ml) for 2 hours and the solution filtered. The filtrate may be refrigerated for storage over a molecular sieve (type 3A). (b) Preparation of indole-3-acetic acid benzyl ester 2

Indole 3-acetic acid 1 (9.45 g, 0.054 mol) was dissolved in methanolic benzyl diethyl anilinium hydroxide (0.54 mol) and the solvent removed in vacuo. The oily residue of the benzyl dimethyl anilinium salt was agitated with benzene, the benzene evaporated and the salt refluxed in toluene (170 ml, 1 h). Traces of unreacted acid and dimethyl aniline by-product were removed by extracting the toluene solution with water, dilute hydrochloric acid (1N) and water. The organic layer was dried over sodium sulphate and concentrated in vacuo to obtain the crude product. Final purification was obtained by crystallization in EtOAc:Hexane to give 11.52 g (80%) indole-3-acetic acid benzyl ester 13 as white crystals (melting point 71°-72° C.); IR (Nujol, cm$^{-1}$); 3 400, 1, 720; $^1$H-NMR (CDCl$_3$, δ): 3.8 (s, 2H), 5.1 (s, 2H) 6.8-8.0 (m, 1H).

(2) Preparation of 1-$^t$Boc-indole-3acetic acid benzyl ester 3

11.52 g (0.046 mol) of indole-3-acetic acid benzyl ester 2, 10.1 g di-tert-butyl dicarbonate (0.046 mol) and 0.56 g (0.0046 mol) dimethyl amino pyridine in 80 ml acetonitrile were stirred for 10 minutes at room temperature, followed by refluxing for 30 minutes. The acetonitrile was evaporated and the residue was extracted with ether, dilute HCl (1N) and water. The ether layer was washed with sodium bicarbonate solution and dried over sodium sulphate. The organic layer was concentrated in vacuo to obtain pure 1-$^t$Boc-indole-3-acetic acid benzyl ester 3 as a yellow-orange oil (15.78 g), 100%); IR (Nujol, cm$^{-1}$) 2 950-3 050; 1 750-1 715; $^1$H-NMR (CDCl$_3$, δ): 1.67 (s, 9H); 3.73 (s, 2H), 5.15 (s, 2H); 6.85-8.2 (m, 11H).

(3) Preparation of N-$^t$Boc-L-aspartic acid 4

522 ml of 1N sodium hydroxide and 34.7 g (0.26 mol) of L-aspartic acid were stirred with cooling at 0° C. 62.8 g of di-t-butyl-dicarbonate (0.26 mol) was then added in one portion and the solid-liquid dispersion was allowed to react at 0°-3° C. until the solid disappeared (150 hours). The reaction mixture was acidified with cold KHSO$_4$ to pH 2. The resulting mixture was extracted twice with EtOAc and the solvent evaporated. The product was recrystallized from ethyl acetate and petroleum ether to yield 32 g of 4 as white crystals (52%); melting point 114°-118° C.

(4) Preparation of N-$^t$Boc-aspartic anhydride 5

32 g of N-$^t$Boc-aspartic acid 4 was dissolved in 430 ml acetic anhydride. The mixture was heated on a water bath at 100° C. for 1.5 hours. The solvent was evaporated and the residue recrystallized from EtOAc and petroleum ether. Yield of 5 26 g (94%); melting point 134°-136° C.

(5) Reaction of 1-$^t$Boc-indole-3-acetic acid benzyl ester 3 with N-$^t$Boc aspartic anhydride 5

A solution of diisopropylamine (2.19 ml) in 50 ml dry THF was stirred in a 100 ml three-necked round-bottomed flask at −78° C. 11.9 ml nBuLi (18.3 mmol) was added through a septum and the reaction was stirred for 10 minutes at −78° C. The acetone bath was removed and the LDA was allowed to form for 30 minutes at room temperature. The LDA was again cooled to −78° C. and the 1-$^t$Boc-indole-3-acetic acid benzyl ester 3 (4.8 g, 13.15 mmol) in 4 ml dry THF was added with a syringe through a septum. The orange solution was then stirred for an additional 20 minutes at −78° C., after which N-$^t$Boc aspartic anhydride 5 (1.41 g, 6.57 mmol) in 15 ml dry THF was added dropwise. After it had been stirred for 1.5 hours at −78° C., the reaction mixture was allowed to warm up to 0° C. and water and HCl (1 N) were added and extracted four times with ether. The solvent was evaporated and the product isolated by flash chromatography (ethyl acetate/hexane/acetic acid: 1/2/0.03). 2.19 g (57%) as a mixture of the two coupling products (6 and 7) was obtained (Rf:0.3; Rf:0.28

(6) Debenzylation of coupling products 6 and 7

A mixture of 6 and 7 (1 g, 1.6 mmol) was dissolved in 30 ml MeOH and 30 mg Pd/charcoal was added, followed by hydrogenation at room temperature (20 Lbs; 1.5 hours). The mixture was filtered through Celite and concentrated in vacuo. Flash chromatography (EtOAc:Hexane/acetic acid: 1/2/0.03 as eluant) afforded 0.30 g of 8 (Rf 0.30, 41%). 8: $^1$H-NMR (CDCl$_3$, δ) 1.37 (s, 9H), 1.64 (s, 9H), 3.01 (d, 1H), 3.20 (d, 1H); 3.75 (s, 2H), 4.51 (m, 1H); 5.53 (s, 1H), 7.18-8.11 (m, 5H).

(7) Preparation of methyl ester 9

4.48 g diazold (0.02 mol) was dissolved in 80 ml ether. 0.84 KOH was dissolved in 25 ml EtOH (96%). The mixture was placed in a special flask and diazomethane was collected in ether in an Erlenmeyer flask cooled at −78° C. The solution was added to 0.77 g (1.6 mmol) of 8 in MeOH, after which the solvent was evaporated with N$_2$. A quantitative yield of 9 was obtained and used without any further purification. $^1$H-NMR (CDCl$_3$,δ): 1.4 (s, 9H); 1.65 (s, 9H); 3.10 (d, 1H, J=6 Hz); 3.20 (d, 1H, J=6 Hz); 3.65 (s, 3H); 3.70 (s, 2H); 4.55 (m, 1H), 5.50 (d, 1H, J=9 Hz); 7.20-8.25 (m, 5H).

(8) Preparation of a mixture of diastereomers 10 from ketone 9

To a solution of 9 (0.45 g; 0.45 g; 0.97 mmol) in 2 ml dichloromethane, were added catalytic amounts of potassium cyanide (9.7 mg) and 18-crown-6 (9.7 mg). Trimethyl silyl cyanide (0.14 ml; 1 mmol) was then added under nitrogen. The reaction mixture was stirred for 1.5 hours at room temperature. The resulting solution was concentrated in vacuo and reacted without any further purification. HCl gas was then bubbled through the TMSCN adduct for 5 minutes at room temperature and 3 ml concentrated HCl was added. The reaction mixture was then brought to 40° C. and HCl gas was bubbled through the dark blue to black solution for 3 hours while stirring was continued. The flow of gas was then stopped and 3 ml H$_2$O was added. The mixture was then refluxed for 1 hour at 95° C.

The reaction mixture was allowed to cool to room temperature and the solvent and excess HCl were removed under reduced pressure. H$_2$O was again added and the pH was brought to 9 with KOH. The solution was then stirred for 1 hour at room temperature, after which it was treated with activated charcoal. The mixture was filtered through Celite. The resulting light green solution was concentrated in vacuo and flash chromatography (n-butanol/H$_2$O/acetic acid: 6/1/1 as eluant) of the residue afforded a mixture of diastereomers 10 (Rf=0.15; 0.064 g, 22%).

An Amberlite resin (IR-120 (H)) column was used to transform 10 into its ammonia salt. 10 (mixture of diastereomers): $^1$H-NMR (D$_2$O+Acetone): 2.30 (m, 1H); 2.8 (dd (br), 1H); 2.85 (d, 1H, J=15 Hz, benzylic proton, 1st diastereomer); 2.98 (s, (br), 2H benzylic protons, 2nd diastereomer); 3.55 (d, 1H, J=15 Hz; benzylic proton 1st isomer); 4.10 (dd, (br) 1H); 7.35 −8.0 (m, 5H).

The invention accordingly provides an indole compound which is a high intensity sweetener having a sweetness, in terms of recognition threshold values, approximately 800 times sweeter than sucrose, and the invention further provides condensation products of said indole, in the form of a lactone and a lactam, which can be formed and stored at pH's where the indole compound is not favoured, and by suitable adjustment of pH can easily be converted to the indole compound. This compound, used, e.g., with a suitable diluent or carrier, can be used as a sweetener for foods or beverages.

Toxicity test using the Ames Test (Maron DM and Ames BN (1983) Mutation Res. 113, 173-215) using strains TA 98 and TA 100 of *Salmonella typhinurium* indicated no toxicity or mutagenicity of the compound.

With regard to the stereoisomers which can exist at the two chiral centres in the structural formula (III), i.e., at the 1 and 3 positions, X-ray crystallography tests have indicated that the naturally occurring sweet isomer is either an S-S diastereomer or an R-R diastereomer, with the probabilities favouring the S-S diastereomer, as the mixture of diastereomers 10 appears to be a mixture of the S-S and S-R diastereomers, the L-aspartic acid starting material which was used having the S configuration. It is not known at the present stage of testing whether only one of the diastereomers, or both of them, is a high intensity sweetener. The two diastereomers can in principle be separated, e.g., by high pressure liquid chromatography (HPLC). The invention extends however, in particular, to any stereoisomer of formula (III) which has high intensity sweetening powers, and to mixtures of diastereomers which contain at least one diastereomer with such high intensity sweetening powers.

As indicated above, for use as high intensity sweeteners, compounds of formula (III) should be present at concentrations of at least 7 g/kg, which is about 5.6 times sweeter than sucrose, whereas they first become detectable (in distilled ionized water) at threshold concentrations of 0.003 g/kg. It is anticipated that a major potential market for these compounds will be in foods and beverages, including sugar substitutes, in which they will be used in concentrations of about 0.03 g/kg (ten times sweeter than the above threshold concentration)—2.5 g/kg (twice as sweet as sucrose).

More typically concentrations of 0.07-1.5 g/kg will be employed, the preferred range for foods and beverages being about 0.1-1 g/kg, usually 0.15-0.6 g/kg.

Naturally, for persons skilled in the art, it is straightforward to prepare compositions for human consumption using the compounds of formula (III), bearing in mind that they are about 800 times more sweet than sucrose. As a first approximation, a concentration 800 times less than that used for sugar (sucrose) in a food or beverage will be employed, which can then be optimized by routine testing.

Foods, beverages and sugar substitutes containing the compounds of formula (III) are expected to be used by persons who experience dietary difficulties with sucrose and related sugars such as fructose, lactose, glucose etc, e.g. for medical reasons. Thus diabetic foods and beverages can make use of compounds of formula (III) as sweeteners, and the same or similar foods or beverages can be of importance in the health-food market, as sugar-free foods and beverages, e.g. for slimming and weight-loss use by persons who are not obliged to avoid sugar for medical reasons.

By way of a generalized example, selected foods and beverages are listed hereunder, giving typical sucrose concentrations employed therein, and the expected concentrations (about 800 times less) in which compounds of formula (III) will be used therein.

| Composition (Food or Beverage) | Typical Sucrose Concentration g/kg | Expected Concentration for Compound of Formula (III) g/kg |
|---|---|---|
| Carbonated Soft Drinks | 120–130 | 0.14–0.16 |
| Soft Drink Powders | 200–300 | 0.25–1.0 |
| Instant Desserts | 500–600 | 0.6–0.8 |
| Jellies and Desserts | 120–160 | 0.14–0.18 |
| Preserved fruit, jams | 100–140 | 0.14–0.55 |
| and preserves Biscuits and Cookies | 150–450 | 0.2–0.55 |

As a sugar substitute, admixed with a suitable granular, e.g. crystalline, carrier, compounds of formula (III) are expected to be used in concentrations of 1-1.5 g/kg, e.g. 1.25 g/kg, to make a free flowing composition which can be used in the same proportions as sucrose, or which in similar fashion can be made in lump form.

As the Applicants have extracted compounds of formula (III) from the roots of Schlerochiton ilicifolius using boiling water, after which the compounds of formula (III) have retained their sweet taste, the Applicant believes that these compounds promise to be sufficiently stable at the temperatures normally encountered in the preparation of preserves, and in the baking of cakes, biscuits, cookies and the like, to have utility in applications in which certain other sugar substitutes cannot be used.

Accordingly, the invention provides compositions which are typically edible or potable, and compositions in which, apart from the compound of formula (III), all other constituents are from among those generally recognized as being edible or potable, the compound of formula (III) being added to said other constituents to impart a sweet taste and thereby sweeten said compositions.

It follows that the present invention also provides a method of sweetening a composition for human consumption, such as an edible or potable composition, by adding thereto a compound of formula (III) in the aforesaid proportions of about 0,003 g/kg up to 7 g/kg or more.

What is claimed is:

1. A composition for human consumption which has a sweet-tasting constituent which is the stereoisomer found in the roots of the plant Schlerochiton ilicifolius of a compound of the formula (III):

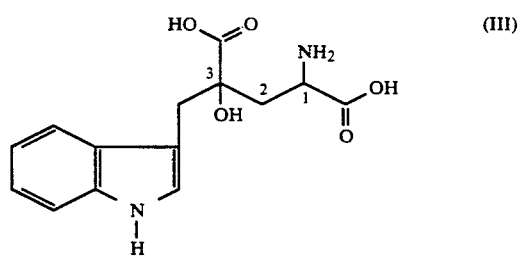

and which compound is 3-(1-amino-1,3-dicarboxy-3-hydroxy-but-4-yl)-indole, or a physiologically acceptable salt of said stereoisomer at the 1 and/or 3 positions, or a derivative of said stereoisomer which is an internal condensation product thereof selected from the group consisting of the lactone of the formula (IV):

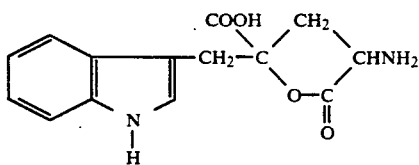

and the lactam of the formula (V):

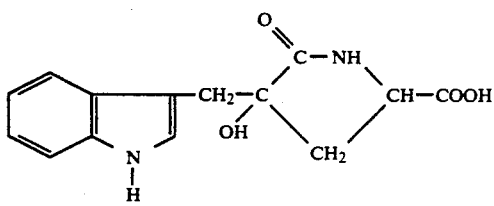

all other constituents of said composition being selected from materials generally accepted as edible or potable.

2. A composition as claimed in claim 1, which is substantially free of water-inextractable material from said roots.

3. A composition as claimed in claim 1, which is substantially free of solvent-extractable material from said roots other than said compound of formula (III).

4. A composition as claimed in claim 1, which is substantially free of water-extractable material from said roots other than said compound of formula (III).

5. A composition as claimed in claim 1, in which the compound is said 3-(1-amino-1,3-dicarboxy-3-hydroxy-but-4-yl)-indole of formula (III).

6. A composition as claimed in claim 1, in which the compound is a physiologically acceptable salt at the 1 and/or 3 positions of said 3-(1-amino-1,3-dicarboxy-3-hydroxy-but-4-yl)-indole of formula (III) and is a salt selected from the group consisting of the ammonium, alkylammonium, sodium, potassium, calcium and magnesium salts thereof.

7. A composition as claimed in claim 1, in which the compound is a derivative of said 3-(1-amino-1,3-diacarboxy-3-hydroxy-but-4-yl)-indole of formula (III), and is a condensation product thereof selected from the group consisting of the lactone of the formula (IV):

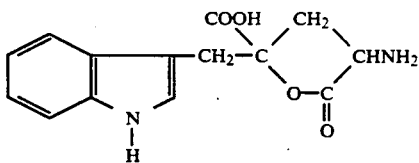

and the lactam of the formula (V):

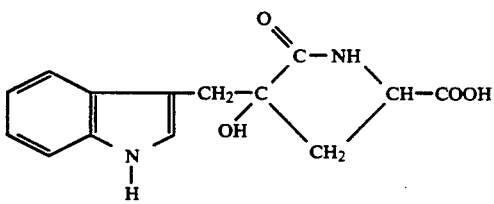

8. A composition as claimed in claim 1, which comprises the S-S diastereomer of said compound with regard to the chiral centres at the 1 and 3 positions.

9. A composition as claimed in claim 1, which comprises the R-R diastereomer with regard to the chiral centres at the 1 and 3 positions.

10. A composition as claimed in claim 6, in which the salt is selected from the sodium and potassium salts of said indole of formula (III).

11. A composition as claimed in claim 6, in which the salt is selected from the calcium and magnesium salts of said indole of formula (III).

12. A composition as claimed in claim 1, in which the concentration of said compound of formula (III) is 0.03-2.5 g/kg.

13. A composition as claimed in claim 12, in which the concentration of the compound of formula (III) is 0.07-1.5 g/kg.

14. A composition as claimed in claim 13, in which the composition is a food or beverage and the concentration of said compound of formula (III) is 0.1-1 g/kg.

15. A composition as claimed in claim 13, in which the composition is a sugar substitute and the concentration of said compound of formula (III) is 1-1.5 g/kg.

16. A composition as claimed in claim 1, which is substantially free of organic solvent-inextractable material from said roots.

17. A composition as claimed in claim 1, which is a food or beverage selected from the group consisting of carbonated soft drinks, soft drink powders, instant desserts, jellies and desserts, preserved fruit, jams and preserves, cakes, biscuits and cookies, and confectioneries and sweetmeats.

18. A composition as claimed in claim 1, which is substantially free of solvent-inextractable material from the roots of the plant Shlerochiton ilicifolius.

19. A composition as claimed in claim 1, in which the concentration of the steroisomer in the composition is at least 0.003 g/kg.

20. A composition as claimed in claim 19, in which the concentration of the stereoisomer is 0.03-2.5 g/kg.

21. A composition for human consumption which has a sweet-tasting constituent which is a physiologically acceptable salt at the 1 and/or 3 positions of a compound of the formula (III):

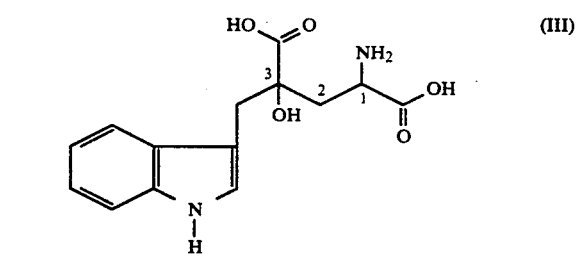

and which compound is 3-(amino-1,3-dicarboxy-3-hydroxy-but-4-yl)-indole, the salt being selected from the group consisting of the ammonium, alkylammonium, sodium, potassium, calcium and magnesium salts of said compound of formula (III).

22. A composition as claimed in claim 21, in which the salt is selected from the sodium and potassium salts of said indole of formula (III).

23. A composition as claimed in claim 21, in which the salt is selected from the calcium and magnesium salts of said indole of formula (III).

24. A composition for human consumption which has a sweet-tasting constituent which is a derivative of a compound of the formula (III):

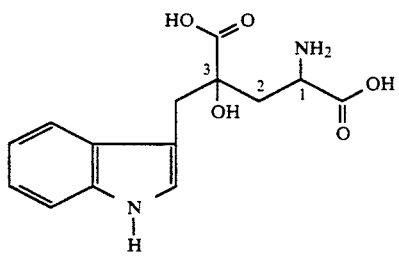

and which compound is 3-(1-amino-1,3-dicarboxy-3-hydroxy-but-4-yl)-indole, the derivative being an internal condensation product of said compound of formula (III) selected from the group consisting of the lactone of the formula (IV):

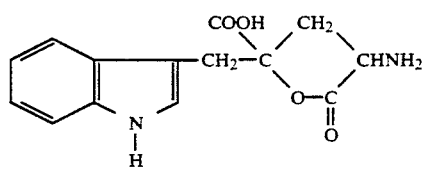

and the lactam of the formula (V):

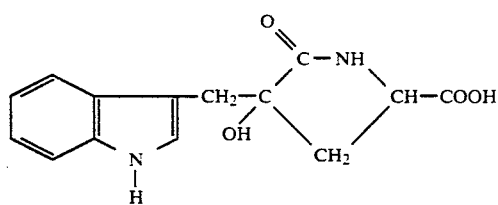

25. A composition for human consumption which has a sweet-tasting constituent which is the S-S diastereomer of a compound of the formula (III):

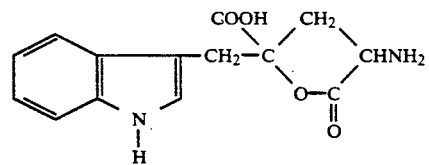

and which compound is 3-(1-amino-1,3-dicarboxy-3-hydroxy-but-4-yl)-indole, or a physiologically acceptable salt of said diastereomer at the 1 and/or 3 positions, or a derivative of said diastereomer which is an internal condensation product thereof selected from the group consisting of the lactone of the formula (IV):

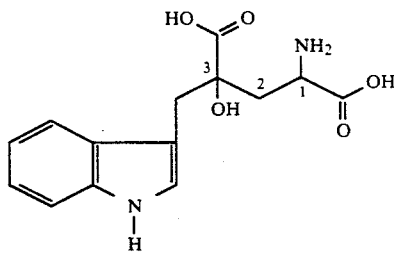

and the lactam of the formula (V):

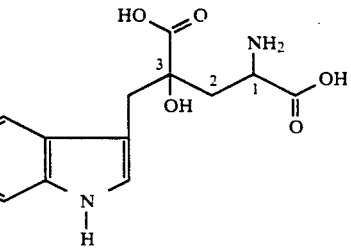

all other constituents of said composition being selected from materials generally accepted as edible or potable.

26. A composition for human consumption which has a sweet-tasting constituent which is the R-R diastereomer of a compound of the formula (III):

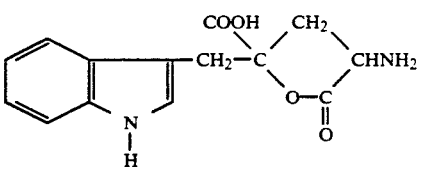

and which compound is 3-(1-amino-1,3-dicarboxy-3-hydroxy-but-4-yl)-indole or a physiologically acceptable salt of said diastereomer at the 1 and/or 3 positions, or a derivative of said diastereomer which is an internal condensation product thereof selected from the group consisting of the lactone of the formula (IV):

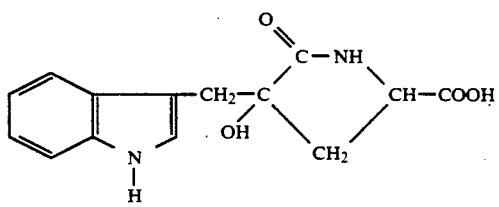

and the lactam of the formula (V):

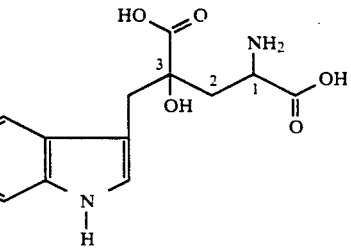

all other constituent of said composition being selected from materials generally accepted as edible or potable.

* * * * *